(12) United States Patent
Al-Ali

(10) Patent No.: US 8,981,926 B2
(45) Date of Patent: Mar. 17, 2015

(54) MONITORING SYSTEM FOR SUDDEN INFANT DEATH SYNDROME FOR BLIND AND DEAF PARENTS

(71) Applicant: Salah Abdullah Al-Ali, Newcastle Upon Tyne (GB)

(72) Inventor: Salah Abdullah Al-Ali, Newcastle Upon Tyne (GB)

(*) Notice: Subject to any disclaimer, the term of this patent is extended or adjusted under 35 U.S.C. 154(b) by 288 days.

(21) Appl. No.: 13/740,220

(22) Filed: Jan. 13, 2013

(65) Prior Publication Data
US 2013/0181833 A1 Jul. 18, 2013

(51) Int. Cl.
| | |
|---|---|
| *G08B 21/02* | (2006.01) |
| *G09B 21/00* | (2006.01) |
| *A61B 5/00* | (2006.01) |
| *A61B 5/0205* | (2006.01) |

(52) U.S. Cl.
CPC ............. *G08B 21/0211* (2013.01); *A61B 5/002* (2013.01); *A61B 5/02055* (2013.01); *A61B 5/6824* (2013.01); *A61B 5/741* (2013.01); *A61B 5/7455* (2013.01); *G09B 21/003* (2013.01)
USPC .................................. 340/539.12; 340/573.1

(58) Field of Classification Search
CPC ......... G08B 21/021; G08B 25/10; A61B 5/00
USPC ................. 340/539.12, 573.1, 539, 825.15, 340/825.54, 573, 825.06; 600/301, 310
See application file for complete search history.

(56) References Cited

U.S. PATENT DOCUMENTS

| | | | |
|---|---|---|---|
| 5,771,001 | A | 6/1998 | Cobb |
| 5,938,619 | A | 8/1999 | Dogre Cuevas |
| 6,498,652 | B1 | 12/2002 | Varshneya et al. |
| 2006/0189872 | A1 | 8/2006 | Arnold |
| 2007/0287923 | A1 | 12/2007 | Adkins et al. |

FOREIGN PATENT DOCUMENTS

| | | | | |
|---|---|---|---|---|
| FR | 2842692 | | 1/2004 | |
| GB | 2138616 | | 10/1984 | |
| GB | 2346217 | * | 8/2000 | ............... A61B 5/00 |
| GB | 2442537 | | 4/2008 | |
| GB | 2447237 | | 9/2008 | |
| GB | 2485690 | | 5/2012 | |
| GB | 2488104 | | 8/2012 | |
| WO | WO 96/36301 | | 11/1996 | |
| WO | WO 96/38080 | | 12/1996 | |
| WO | WO 2009/049104 | | 4/2009 | |

* cited by examiner

*Primary Examiner* — Steven Lim
*Assistant Examiner* — Kaleria Knox
(74) *Attorney, Agent, or Firm* — Richard C. Litman

(57) ABSTRACT

A monitoring system for sudden infant death syndrome alerts parents, including parents who are blind and deaf, of changes in their infant's health condition. The system comprises three parts: a portable monitoring and warning control unit, a sensor bracelet that would be placed around the infant's wrist and an alarm bracelet for blind and deaf parents. The infant sensor bracelet comprises multiple sensors and a microphone and transceiver to receive and transmit data to a portable control monitoring unit. A similar system is provided for blind and deaf parents. The vibration alarm units each have Braille characters printed in the top to enable a blind person to identify the vibration alarm. A portable monitoring and warning control unit comprises at least a transceiver to communicate with the bracelets and a processing control unit to collect data and compare it with thresholds/acceptable ranges.

18 Claims, 6 Drawing Sheets

MONITORING SYSTEM FOR SUDDEN INFANT DEATH SYNDROME FOR BLIND AND DEAF PARENTS

CROSS-REFERENCE TO RELATED APPLICATION

This application claims the benefit of United Kingdom Patent Application No. 1200530.2, filed Jan. 12, 2012, published as GB2485690 on May 23, 2012.

BACKGROUND OF THE INVENTION

1. Field of the Invention

The present invention relates to a monitoring system for sudden infant death syndrome alerts parents, including parents who are blind and deaf, of any unexpected and unpleasant change in their infant's health condition, especially at night time.

2. Description of the Related Art

Every year thousands of babies die of premature crib death, also known as Sudden Infant Death Syndrome. While some of them inherited some problems such as heart irregularities or respiratory distress, other deaths are caused by accidents such as suffocation from blankets or pillows and lack of attention to certain readily observable conditions such as body temperature due to illness. In almost all cases, early detection can save the infants from death. Even though the probability of such tragedies happening is relatively small, most parents and caretakers are eager to acquire a device that will help them to further minimize the chance of suffocation if the device is inexpensive and easy to use.

There are some relevant documents to monitoring sudden infant death syndrome of infants. For example the GB patent GB2447237 which describes a baby heartbeat monitoring device to prevent cot death comprises a wrist band 4 to be attached to the baby's wrist, an electrode sensor 3 to measure pulse rate, and a lithium battery 2. If a change in heartbeat is detected the wristband wirelessly transmits an alarm signal to a remote receiver device 8 where an audible alarm is sounded.

Further the GB patent GB2442537 which describes The Wireless Skin Temperature monitoring device consists of two devices. The first device is an adjustable waterproof silicone arm band 3, worn on a baby's upper-arm, housing a temperature sensor 1, microprocessor, RF transmitter and power source 5 which will send the temperature data to the other device. Popper fixings 2, 4 are used to secure the band around the arm. The second device is a receiver device 7, also made from silicone 6 and worn on the wrist of a carrier or parent, housing an RF Receiver, microprocessor, power source and LCD Module 7 displaying the temperature reading or digital time. When pre-defined temperatures are reached an alarm will sound and the LCD will change color, blue for cold, and red for hot. If extreme temperatures are reached the LCD display will flash the respective color and will sound a louder more rapid alarm. The LCD will also display a wireless signal strength indicator and display the time. A wireless on/off reset button 8 is featured to switch off any alarm. A Time set button 9 is featured to set hour and minutes on the receiving device.

In addition, the GB patent GB2346217 describes a detection device capable of being coupled to a person for remotely monitoring heart and respiratory functions includes a processor, a photo cell coupled to the processor for determining blood oxygen content of the person and a temperature sensor coupled to the processor for determining a temperature of the person. The processor compares the determined blood oxygen content and the temperature to desired values. A transmitter is included for transmitting a warning signal if one of the determined blood oxygen content and the temperature are other than the desired values. The device is battery powered and transmits signals at radio frequencies. The warning may be visual or audible.

Therefore, a need exists for providing a system for early warning to allow quick response to signs of suffocation in infants or other people who are unable to help themselves. Such a system could save thousands of lives every year. A further need exists for early detection of progressing illness which may relieve parents or caretakers some of the stress and effort in monitoring people under their care.

SUMMARY OF THE INVENTION

This invention describes a monitoring system for sudden infant death syndrome comprises portable warning and monitoring control unit and electronic bracelets.

DETAILED DESCRIPTION OF THE PREFERRED EMBODIMENTS

The invention describes a monitoring system for sudden infant death syndrome for blind and deaf parents comprises portable warning and monitoring control unit and electronic bracelets.

As Shown in FIGS. 1,2,3,4,5,6,7,8,9 the warning and monitoring control unit for Sudden Infant Death Syndrome alert parents (include those parents who are blind and death) on any unexpected and unpleasant change in their infant health condition, especially at night time, and consist of three parts.

Figure 1:
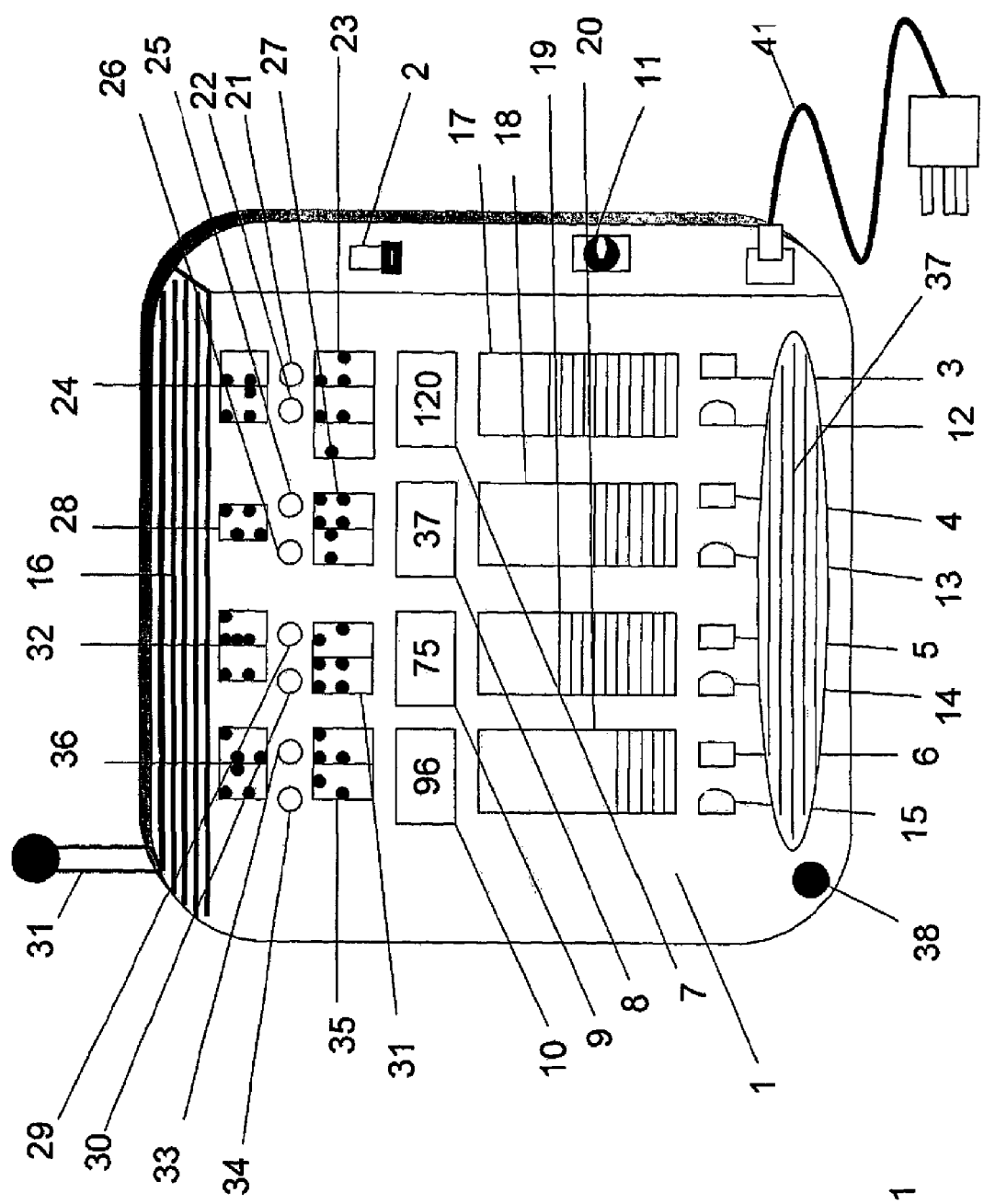
FIG. 1 describes the monitoring control unit from the front side.
Figure 2:
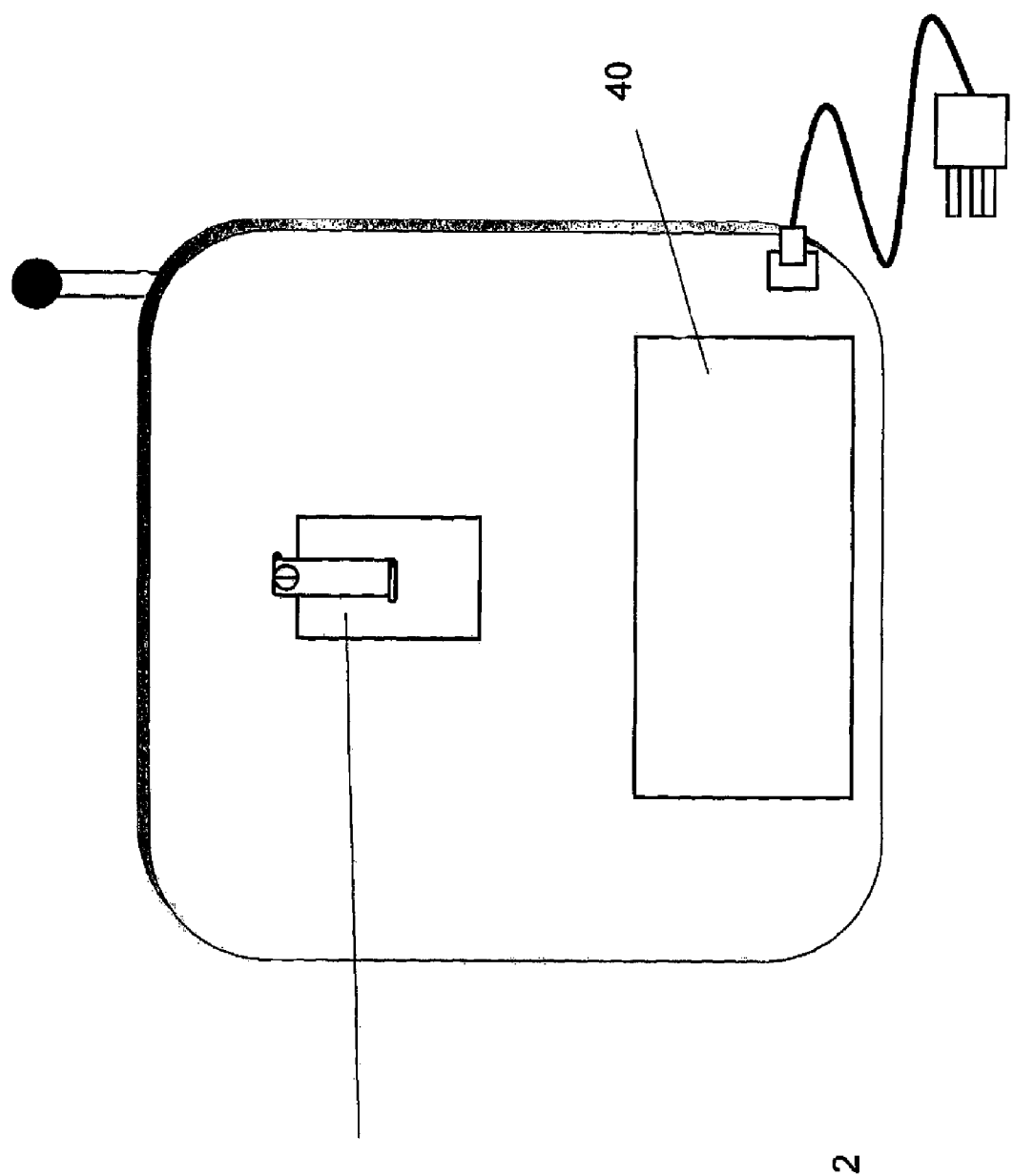
FIG. 2 describes the monitoring control unit from the back side.

As shown in FIGS. 1&2 the first part is the portable warning and monitoring control unit that has an antenna (31), a power switch (2) that can be pressed in to switch "on" portable warning and monitoring control unit (1), and release out to switch "off" the portable warning and monitoring control unit, four speakers (3,4,5,6) each speaker has its unique and different tones that alert the parents through a sound alarm when either infant heart beating rate (7), temperature reading (8), blood pressure reading (9), and oxygen saturation (10) level falls below or exceeds the normal reading. The four speakers are contacted to a sound control switch (11) to lower or increase the sound (good for those parents who have hearing problems). The portable warning and monitoring control unit has also four separate buttons (12,13,14,15). When pressed the first button (12) parents would hear a voice stating the exact reading for infant heart beating. When pressed the second button (13) parents would hear the exact reading for infant temperature. When the third button is pressed (14) parent would hear the exact reading for infant blood pressure.

When pressed the fourth button (15) parents would hear the exact reading for infant oxygen saturation. This would enable parents, especially who are blind parents, to monitor their infant health conditions.

The portable warning and monitoring control unit has also a horizontal hard plastic coat cover the front top side of the portable warning monitoring control unit (16) to protect the screens and reading cells from being damaged when the unit accidentally falling face down on a hard floor. The portable warning and monitoring control unit has also four screens (17,18,19,20). The first screen shows infant heart beating rate (17), with green light (21) to indicate that measuring infant heart beating reading is in progress, warning red light (22) to indicate "very low" or "exceed" in infant heart beating reading. Numerical reading and Braille numbers/codes for infant heart beating rate level located above the first screen (7, 23). An abbreviation of heart beating (HP) is printed in a Braille letters/characters above the first screen (24). This would help blind and death parents to identify the first screen as for infant heart beating. A Braille letters/characters is designed for those parents who are blind and death.

The second screen shows infant temperature level (18), with green light (25) to indicate that measuring infant temperature level is in progress, warning red light (26) to indicate "very low" or "high" in infant temperature level. Numerical reading and Braille numbers/codes for infant temperature level (8, 27) located above the second screen (28). An abbreviation of infant temperature (T) is printed in a Braille letters/characters above the second screen. This would help blind and death parents to identify the first screen as for infant temperature. The third screen shows infant blood pressure level (19), with green light (29) to indicate that infant measuring air pressure level is in progress, warning red light (30) to indicate any "very low" or high" in infant blood pressure level. Numerical reading and Braille numbers/codes for infant blood pressure level (9, 31) located above the third screen. An abbreviation of infant blood pressure (BP) is printed in a Braille letters/characters above the third screen (32). This would help blind and death parents to identify the first screen as for infant blood pressure. The fourth screen shows infant oxygen saturation level (20), with green light (33) to indicate that infant measuring oxygen saturation level is in progress, warning red light (34) to indicate any "very low" or high" in infant oxygen saturation level. Numerical reading and Braille numbers/codes for infant oxygen saturation level (10,35) located above the fourth screen (36). An abbreviation of infant oxygen saturation (OS) is printed in a Braille letters/characters above the fourth screen. This would help blind and death parents to identify the first screen as for infant oxygen saturation.

The portable warning and monitoring control unit has also processing control unit has processor to collect data and compare it with the default values (not shown in the figures), and memory to store reading data from the three sensors (not shown in the drawings). The portable warning and monitoring control unit has also a speaker (37) receive infant voice and unusual infant movements from the sensitive microphone build into the infant bracelet. The portable warning and monitoring control unit speaker has also a switch (38) that can be pressed in to switch on' the speaker and release out to switch off the speaker. The portable warning and monitoring control unit has also a hanger (39) that allow parent to monitor infant health condition throughout the house, rechargeable battery case (40) electricity connection (41).

Figure 3:
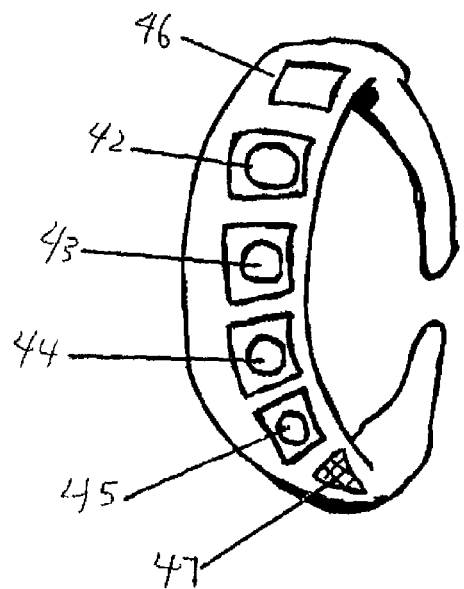
FIGS. 3 & 4 describes electronic bracelet designed for infant.
Figure 6:
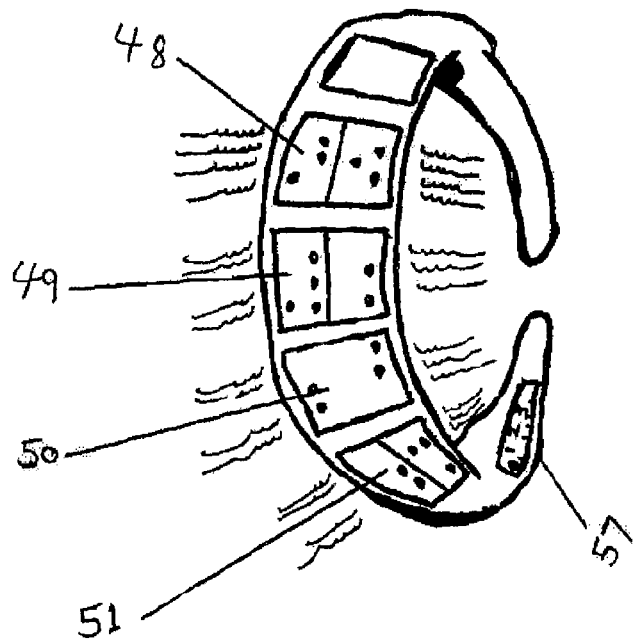
Figure 7:
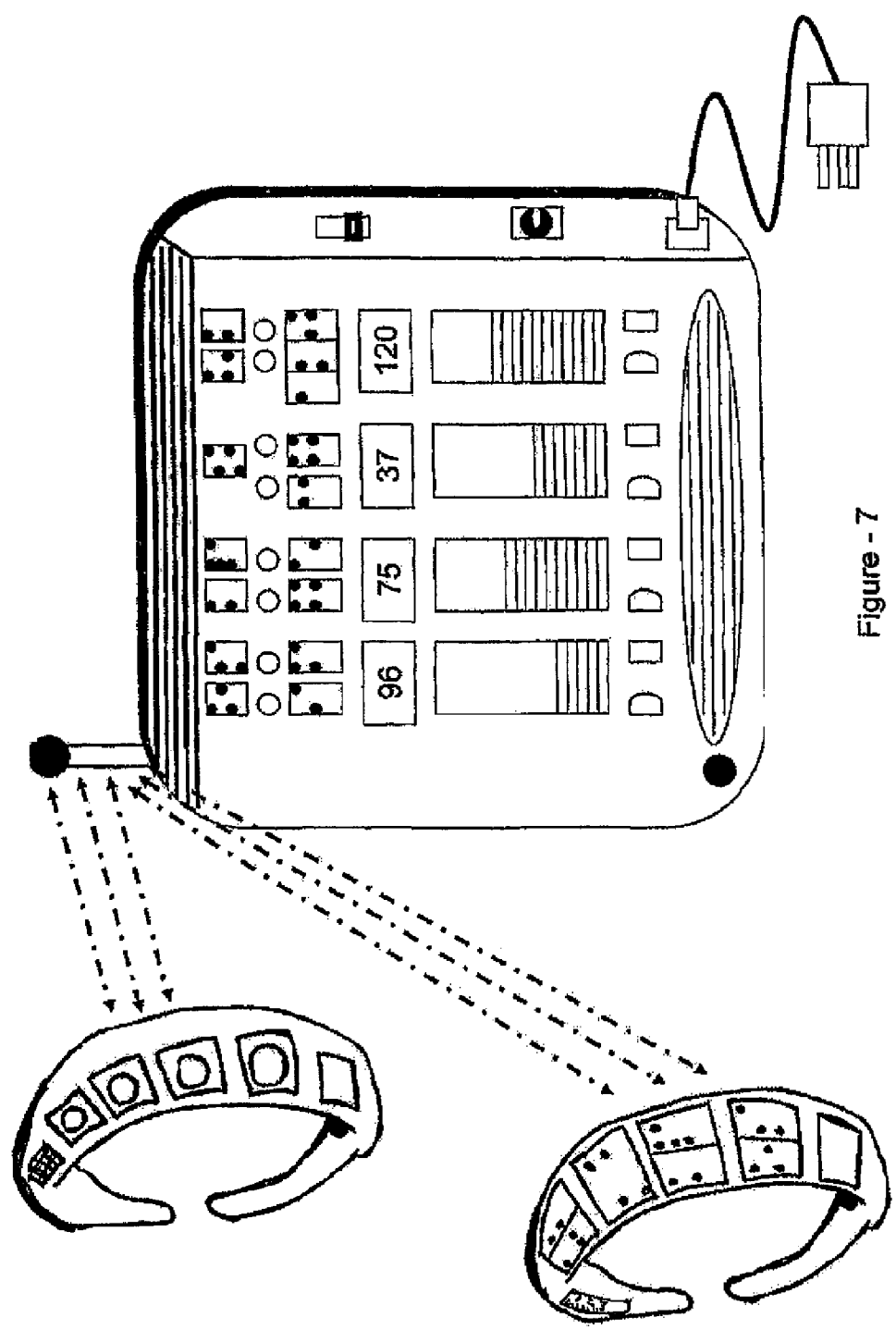
FIG. 7 describes communication method between the electronic bracelets (designed for infant and the other designed for blind and death parents) and the monitoring control unit.

As Shown in FIG. 3, the second part is the electronic bracelet made of elastic waterproof material that would be placed around the infant arm (FIG. 6). The electronic bracelet consists of heart beating sensor (42), temperature sensor (43), blood pressure sensor (44), oxygen saturation sensor (45) supported rechargeable battery (46), processing unit to collect data from the four sensors (not shown in the drawing), and transceiver to receive and transmit data between the bracelet processing unit and the main portable control monitoring unit (not shown in the drawing). The four sensors in the bracelet can be activated by pressing the concern sensor (FIG. 4, No. 43), and deactivated when releasing the same sensor.

The bracelet has also a sensitive microphone (FIG. 3, No. 47) which would detect infant voice and infant unusual movements and then transfer infant voice and infant unusual movements to the speaker already build into the portable warning and monitoring control unit (FIG. 1, no. 37). This would allow the parents to hear their infant voice and unusual movements from distance.

Figure 4:
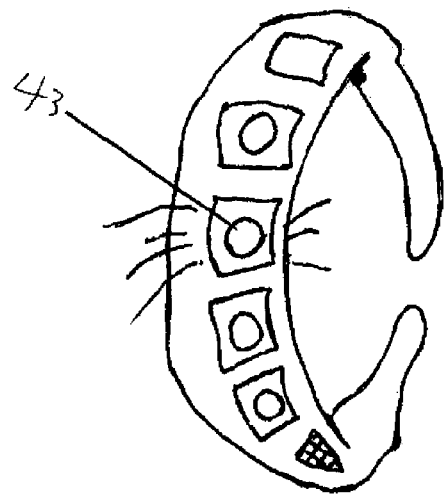
Figure 8:
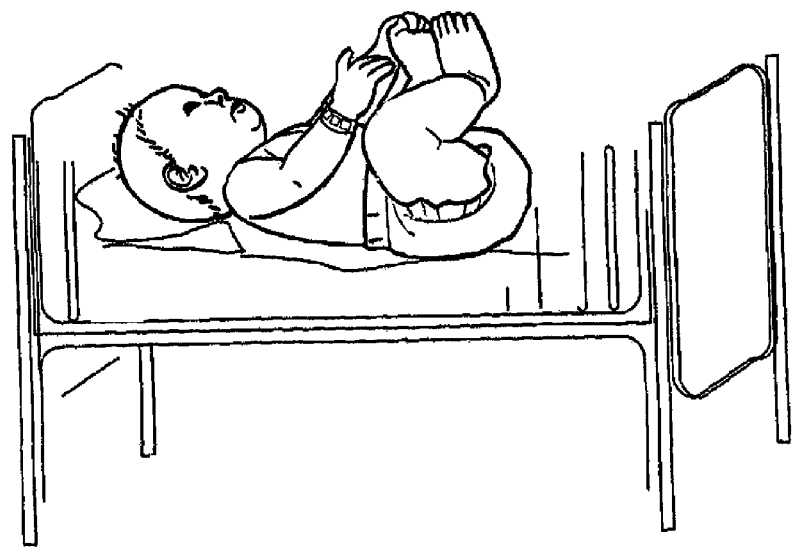
FIG. 8 describes infant wear the bracelet in his hand.
Figure 9:
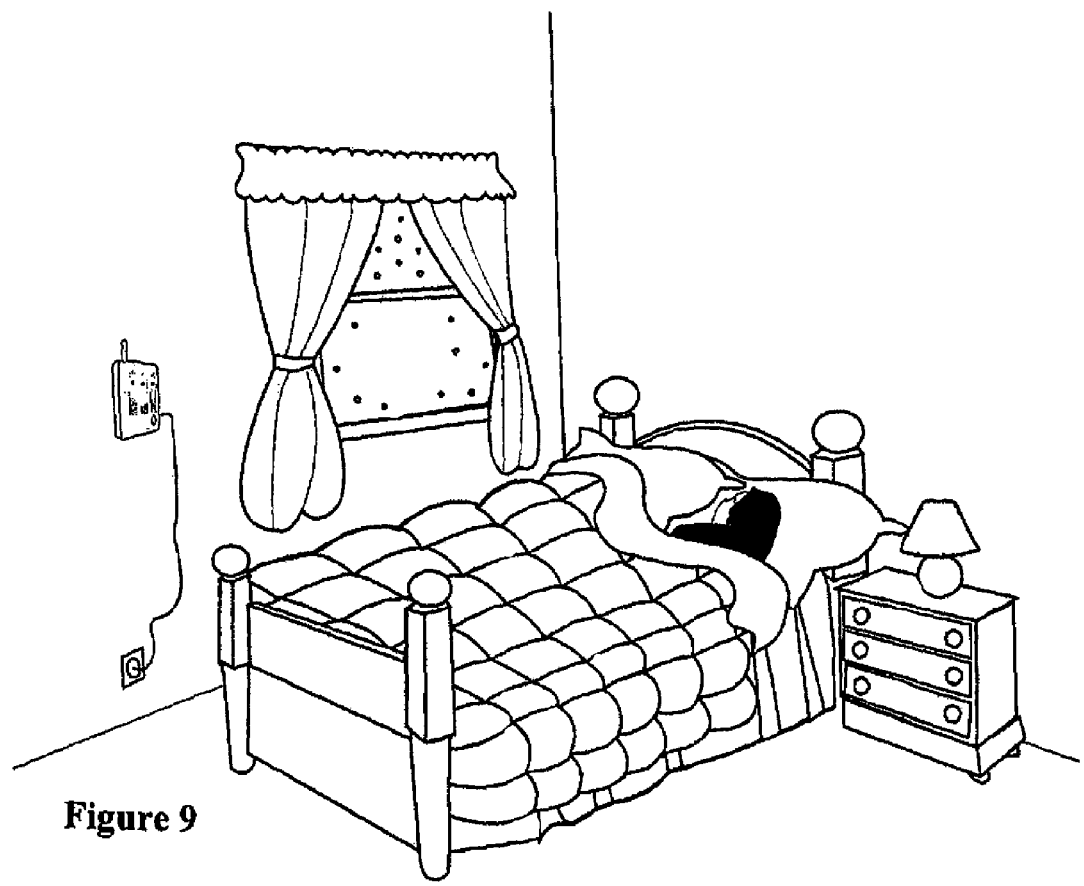
FIG. 9 describes the monitoring control unit while it is hanged in the wall.

To operate monitoring system for sudden infant death syndrome, the portable warning and monitoring control unit has to be switched "on" by pressing the switch in the control panel (FIG. 1, No. 2), automatically green lights for heart beating reading indicator (FIG. 1, No. 21), temperature reading indicator (FIG. 1, No. 25), blood pressure indicator (FIG. 1 No. 29), and oxygen saturation indicator (FIG. 1, No. 33) would all be appear. This indicates that the control panel (FIG. 1, No. 1) is ready to receive information, through the antenna (FIG. 1, No. 31) from the bracelet that is attached around the infant arm (FIG. 8). On the other hand, the four sensors in the bracelet can be activated by pressing the concern sensor (FIG. 4, No. 43), and deactivated when releasing the same sensor. In other word, when infant temperature sensor is pressed for example at the bracelet the infant temperature sensor would light to indicate that is activated "on" (FIG. 4, No. 43). However, when releasing the same sensor (infant temperature sensor) the light would disappear to indicate that the temperature sensor is deactivating "off". The first information the bracelet would send is infant heart beating condition (FIG. 3, No. 42). The second information the bracelet would send is infant temperature condition (FIG. 3, No. 43). The third information the bracelet would send is infant blood pressure condition (FIG. 3, No. 44). The fourth information the bracelet would send is infant oxygen saturation condition (FIG. 3, 45). The control panel would then display the level of infant heart beating (FIG. 1, No. 17) with numerical and a Braille numbers/codes for infant heart beating reading (FIG. 1, No. 7, 23), infant temperature level (FIG. 1, No. 18), with numerical and a Braille numbers/codes for infant temperature reading (FIG. 1, No. 8, 27), infant blood pressure level (FIG. 1, No. 19), with numerical and a Braille numbers/codes for infant blood pressure reading (FIG. 1, No. 9, 31), and infant oxygen saturation reading (FIG. 1, No. 20), with numerical and a Braille numbers/codes for infant oxygen saturation reading (FIG. 1, No, 10, 35).

In the case when infant heart beating reading falls "below" or exceeds" the normal reading (100-130), a red light would appear (FIG. 1, No. 22) companies with a sound warning (FIG. 1, No. 3) to alert the parents of such unpleasant change in their infant heart beating reading. In the case when infant temperature reading falls "below" or exceeds" the normal reading (37 cent grate), a red light would appear (FIG. 1, No. 26) companies with a sound warning (FIG. 1, No. 4) to alert the parents of such unpleasant change in their infant temperature reading. In the case when infant blood pressure reading falls "below" or exceeds" the normal reading (70-8 5), a red light would appear (FIG. 1, No. 30) companies with a sound warning (FIG. 1, No. 5) to alert the parents of such unpleasant change in their infant blood pressure reading. In the case when infant oxygen saturation reading falls "below" or exceeds" the normal reading (96-97), a red light would appear (FIG. 1, No. 34) companies with a sound warning (FIG. 1, No. 6) to alert the parents of such unpleasant change in their infant oxygen saturation reading.

Figure 5:
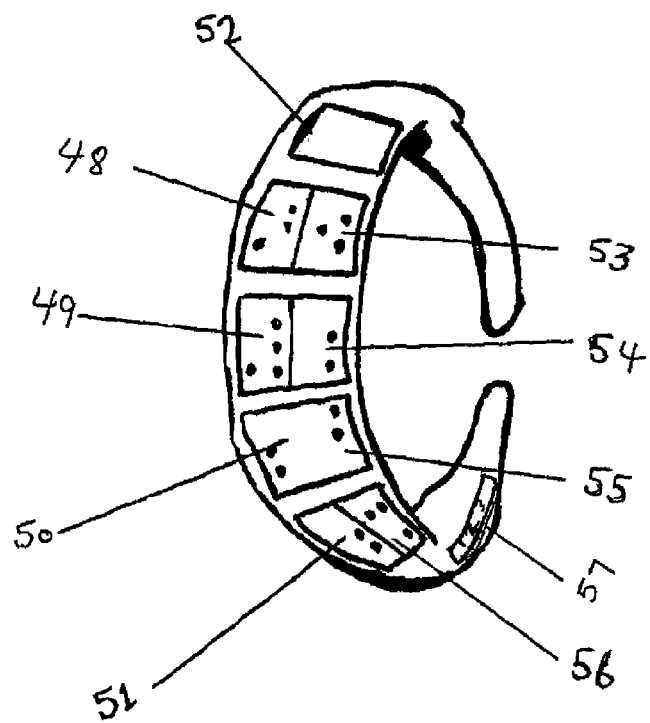
FIGS. 5 & 6 describes electronic bracelet designed for blind and death parents.

As Shown in FIG. 5, the third part is the electronic bracelet made of elastic waterproof material put around the wriest of the blind and death parents (FIG. 5,6). The electronic bracelet consists of heart beating vibrated device (48), temperature vibrated device (49), blood pressure vibrated device (50), oxygen saturation vibrated device (51) supported by rechargeable battery (52), processing unit to collect data from the four sensors (not shown in the drawing), and transceiver to receive and transmit data between the bracelet processing unit and the main portable control monitoring unit (not shown in the drawing). Each of the four vibrated devices is identified by using an abbreviation letter using a Braille characters printed on the top of each device for identification. For example, printed the letters (MB) on the top of the first vibrated device, using a Braille characters, to indicate that this vibrated device for infant heat beating (FIG. 5, No. 53). Printed letter (T) on the top of the second vibrated device, using Braille characters, to indicate that this vibrated device is for infant temperature level (FIG. 5, No. 54), printed letters (BP) on the top of the third vibrated device, using a Braille characters, to indicate that this device is for infant blood pressure (FIG. 5, No. 55), printed letters (ox) on the top of the fourth vibrated device, using a Braille characters, to indicate that this device is for infant oxygen saturation (FIG. 5, No. 56. All abbreviations letters are printed in the Braille characters/letters which are designed for those parents who are blind and death.

In the case when infant heart beating reading falls "below" or exceeds" the normal reading (100-130), the device marked with the letter (FIB) would vibrate to alert the parents, especially while parents are sleeping, to take the right action (FIG. 6, No. 48). In the case when infant temperature reading falls "below" or exceeds" the normal reading (37 cent grate), the device marked with the letter (T) would vibrate to alert the parents, especially while parents are sleeping, to take the right action (FIG. 6, No. 49). In the case when infant blood pressure reading falls "below" or exceeds" the normal reading (70-85), the device marked with the letter (BP) would vibrate to alert the parents, especially while parents are sleeping, to take the right action (FIG. 6, No. 50). In the case when infant oxygen saturation reading falls "below" or exceeds" the normal reading (96-97), the device marked with the letter (ox) would vibrate to alert the parents, especially while parents are sleeping, to take the right action (FIG. 6, No. 51).

The bracelet which is designed for parent who are blind and death has also a switch with three indicators marked 1, 2 and 3 (FIG. 6, No. 57) to control the volume of vibration. For example No. (I) on the switch means less vibration, no (2) on the switch means medium vibration, and No. (3) on the switch means high vibration.

The Features of the design for which novelty is claimed reside in the shape & configuration of the article as shown in the representations.

I claim:

1. Monitoring system for sudden infant death syndrome for blind and deaf parents comprises:

Bracelet made of elastic waterproof material put around the wriest of the infant comprises four sensor units for heart beating, temperature, blood pressure, and oxygen saturation unit, rechargeable battery, sensitive microphone, processing unit to collect data from the four sensors, and transceiver to receive and transmit data between the bracelet processing unit and the main portable control monitoring unit;

Bracelet made of elastic waterproof material put around the wriest of the blind and death parents comprise four vibrated devices with a Braille characters abbreviation printed in the top of the vibrated device for monitoring heart beating, temperature, blood pressure, oxygen saturation, rechargeable battery, a switch with three indicators marked 1, 2 and 3, to control the volume of vibration, processing unit to collect data from the four vibrated devices, transceiver to receive and transmit data between the bracelet processing unit and the main portable control monitoring unit, four alarm devices for heart beating infant status which produce a vibration when the infant heart beating level falls below or exceed the heart beating normal level, for temperature infant status which produce a vibration when the infant temperature level falls below or exceed the temperature normal level, for blood pressure infant status which produce a vibration when the infant blood pressure level falls below or exceed the blood pressure normal level, and for oxygen saturation infant status which produce a vibration when the infant oxygen saturation level falls below or exceed the normal oxygen saturation level;

Portable monitoring and warning control unit comprises transceiver to connect the portable monitoring control unit with the bracelets, processing control unit has processor to collect data and compare it with the default values, memory to store reading data from the four sensors, alarm device for heart beating infant status which produce a red light and warning sound in the speaker when the infant heart beating level falls below or exceed the heart beating normal level, alarm device for temperature infant status which produce a red light and warning sound in the speaker when the infant temperature level falls below or exceed the temperature normal level, alarm device for blood pressure infant status which produce a red light and warning sound in the speaker when the infant blood pressure level falls below or exceed the blood pressure normal level, alarm device for oxygen saturation infant status which produce a red light and warning sound in the speaker when the infant oxygen saturation level falls below or exceed the normal oxygen saturation level, four separate screens to display the data collected from the four sensors in the same time in different screen, water proof plastic cover of the control unit has a backside hanger to hang the portable unit anywhere.

2. Monitoring system as in claim 1, where the portable warning and monitoring control unit is operated by both rechargeable battery and electricity.

3. Monitoring system as in claim 1, where the portable warning and monitoring control unit has activation button and can be deactivated by the same button.

4. Monitoring system as in claim 1, where the portable warning and monitoring control unit has four screens and each of the four screens is identified by using Braille letters/characters.

5. Monitoring system as in claim 1, where the portable warning and monitoring control unit has four screens and each one is for separate sensor. And each one has two led to indicate the infant status.

6. Monitoring system as in claim 4, each screen has green light to indicate that sensors reading data is in progress.

7. Monitoring system as in claim 4, each screen has red light to indicate that sensor's reading data is below or exceed the normal level.

8. Monitoring system as in claim 1, where the portable warning and monitoring control unit will show the data collected from the four sensors unit in analog and digital reading.

9. Monitoring system as in claim 1, where the portable warning and monitoring control unit will show the data collected from the four sensors unit in the form of Braille reading.

10. Monitoring system as in claim 1, where the portable warning and monitoring control unit has four speakers to alert the parent and each speaker can has its different and unique tone, so the parent can monitor the status from different ways by different videos in the separate four screens or from the four different tones from the speakers.

11. Monitoring system as in claim 1, where the portable warning and monitoring control unit has four speakers connected to a sound control switch to lower or increase the sound of the four speakers.

12. Monitoring system as in claim 1, where the portable warning and monitoring control unit has four separate buttons: the first button allow parents to hear a voice stating the exact reading for infant heart beating, the second button allow parents to hear the exact reading for infant temperature, the third button allow parent to hear the exact reading for infant blood pressure, the fourth button allow parents to hear the exact reading for infant oxygen saturation.

13. Monitoring system as in claim 1, where the portable warning and monitoring control unit has a speaker to detect infant voice and unusual infant movements from distance through the sensitive microphone build into the infant bracelet.

14. Monitoring system as in claim 1, where the portable warning and monitoring control unit has a horizontal hard plastic coat cover the front top side of the portable warning monitoring control unit to protect the screens and reading cells from being damaged when the unit accidentally falling on a hard floor.

15. Method for monitoring sudden infant death syndrome for blind and deaf parents comprises:
   Activate the portable warning and monitoring control unit to be turned on and to be ready to receive information from the bracelets through its antenna;
   Programming the control processing unit with the default or normal values of the infant heart beating, temperature, blood pressure, and oxygen saturation levels;
   Automatically send request signal from the portable control unit to the bracelets unit to update the portable control unit with the current status of the infant;
   The transceiver of the bracelets send the current status to the control unit;
   The control processing unit compares the reading data of the four sensors with the normal default value, wherein any value exceed or below the normal value, the screen display this values and the red light is on and warning sound will happen.

16. Method for monitoring sudden infant death syndrome as claimed in claim 15 wherein the portable warning and monitoring unit would shows numerical for infant heart beating reading.

17. Method for monitoring sudden infant death syndrome as claimed in claim 15 wherein the portable warning and monitoring unit would show a Braille reading for infant (temperature, blood pressure, oxygen saturation, and heart beating) reading, numerical for infant (temperature, blood pressure, reading, numerical for infant blood pressure, and oxygen saturation) reading.

18. Method for monitoring sudden infant death syndrome as claimed in claim 15 wherein the portable warning and monitoring unit would show and alert the parent through sound and light of any unpleasant change in infant heart beating level when infant heart beating reading falls below or exceed the normal reading, the parent through sound and light of any unpleasant change in infant temperature level when infant temperature reading falls below or exceed the normal reading (37 cent grate), through sound and light of any unpleasant change in infant blood pressure level when infant blood pressure reading falls below or exceed the normal reading (70-85) and through sound and light of any unpleasant change in infant oxygen saturation level when infant oxygen saturation reading falls below or exceed the normal reading (96-97).

* * * * *